United States Patent
Shalaby

(10) Patent No.: US 8,226,683 B2
(45) Date of Patent: *Jul. 24, 2012

(54) HIGH STRENGTH NITROGENOUS CAPROLACTONE COPOLYMERS AND BIOMEDICAL CONSTRUCTS THEREFROM

(75) Inventor: Shalaby W. Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 315 days.

This patent is subject to a terminal disclaimer.

(21) Appl. No.: 10/128,121

(22) Filed: Apr. 23, 2002

(65) Prior Publication Data

US 2002/0155159 A1 Oct. 24, 2002

Related U.S. Application Data

(60) Continuation-in-part of application No. 09/713,860, filed on Nov. 16, 2000, now Pat. No. 6,485,749, which is a division of application No. 09/103,142, filed on Jun. 29, 1998, now Pat. No. 6,197,320, which is a continuation-in-part of application No. 08/660,089, filed on Jun. 3, 1996, now Pat. No. 5,773,563, which is a continuation of application No. 08/212,174, filed on Mar. 11, 1994, now Pat. No. 5,522,842.

(51) Int. Cl.
 *A61B 17/04* (2006.01)
 *A61L 17/00* (2006.01)
(52) U.S. Cl. .................. 606/228; 606/230; 606/231
(58) Field of Classification Search .................. 424/486; 606/228, 230, 231
 See application file for complete search history.

(56) References Cited

U.S. PATENT DOCUMENTS

| | | | | |
|---|---|---|---|---|
| 4,045,418 A | * | 8/1977 | Sinclair | 528/357 |
| 4,057,537 A | * | 11/1977 | Sinclair | 528/354 |
| 4,539,981 A | * | 9/1985 | Tunc | 606/77 |
| 4,624,256 A | * | 11/1986 | Messier et al. | 606/230 |
| 4,700,704 A | * | 10/1987 | Jamiolkowski et al. | 606/230 |
| 4,719,246 A | * | 1/1988 | Murdoch et al. | 521/134 |
| 4,788,979 A | * | 12/1988 | Jarrett et al. | 606/230 |
| 4,791,929 A | | 12/1988 | Jarrett et al. | 128/335.5 |
| 4,994,074 A | | 2/1991 | Bezwada et al. | 606/230 |
| 5,239,002 A | | 8/1993 | Ahmed et al. | 252/150 |
| 5,252,701 A | * | 10/1993 | Jarrett et al. | 528/354 |
| 5,425,984 A | | 6/1995 | Kennedy et al. | 428/229 |
| 5,426,156 A | * | 6/1995 | Bederke et al. | 525/426 |
| 5,468,253 A | * | 11/1995 | Bezwada et al. | 606/230 |
| 5,522,842 A | | 6/1996 | Shalaby | 606/230 |
| 5,543,218 A | * | 8/1996 | Bennett et al. | 428/375 |
| 5,595,751 A | | 1/1997 | Bezwada et al. | 424/422 |
| 5,612,052 A | | 3/1997 | Shalaby | 424/426 |
| 5,633,343 A | | 5/1997 | Bezwada et al. | 528/361 |
| 5,639,851 A | | 6/1997 | Bezwada et al. | 528/354 |
| 5,773,563 A | | 6/1998 | Shalaby | 528/354 |
| 6,197,320 B1 | | 3/2001 | Shalaby | 424/408 |

* cited by examiner

*Primary Examiner* — Zohreh Fay

(74) *Attorney, Agent, or Firm* — McCormick, Paulding & Huber LLP

(57) ABSTRACT

This invention is directed to an absorbable, nitrogenous copolyester composition based on more than 50 percent of $\epsilon$-caprolactone-derived repeat units, having a number average molecular weight of more than $\geq 30$ kDa and its use as (1) an absorbable coating for stents which may also contain a bioactive compound at $\geq 10$ percent loading; (2) an absorbable suture or mesh and similar devices; and (3) plugs for blocking the end of seed needles used in radiation therapy.

3 Claims, No Drawings

HIGH STRENGTH NITROGENOUS CAPROLACTONE COPOLYMERS AND BIOMEDICAL CONSTRUCTS THEREFROM

This application is a Continuation-in-part of U.S. Ser. No. 09/713,860 entitled "Absorbable ε-Caprolactone Copolymers and Medical Devices," filed Nov. 16, 2000 now U.S. Pat. No. 6,485,749, which is a Divisional of U.S. Ser. No. 09/103,142, entitled "Absorbable ε-Caprolactone Copolymers and Medical Devices," filed Jun. 29, 1998, now U.S. Pat. No. 6,197,320, which is a Continuation-in-part of U.S. Ser. No. 08/660,089, entitled "Absorbable ε-Caprolactone Copolymers," filed Jun. 3, 1996, now U.S. Pat. No. 5,773,563, which is a Continuation of U.S. Ser. No. 08/212,174, entitled "Absorbable ε-Caprolactone Copolymers as Suture Coatings Displaying Autocatalyzed Hydrolysis," filed Mar. 11, 1994, now U.S. Pat. No. 5,522,842.

BACKGROUND OF THE INVENTION

Prior applications and pertinent issued patents of the same inventor have dealt with nitrogenous copolymers based primarily of ε-caprolactone and focused on their use as lubricious coatings for medical devices and particularly absorbable suture braids and stents (U.S. Pat. Nos. 5,522,842; 5,773,563; and 6,197,320). Meanwhile, copolymers of this prior art did not exploit the autocatalytic hydrolyzability built-in feature of these polymers, which would be of great value in several applications which have been limited, traditionally, to absorbable polymers having a $T_g \geq 40°$ C. and/or $T_m \geq 90°$ C. and inherent viscosity (I.V.) of $\geq 0.5$. These properties are associated with much higher molecular weight polymers than those required for use as lubricious coatings. This prompted the exploration of high molecular nitrogenous copolyesters based primarily on ε-caprolactone and with improved mechanical properties to allow their use in more demanding, unanticipated biomedical applications. This invention relates to the synthesis of novel, high molecular weight, nitrogenous copolyesters based primarily on ε-caprolactone and their use for the production of and use in several biomedical and pharmaceutical applications.

SUMMARY OF THE INVENTION

The present invention is directed to a high molecular weight, crystalline nitrogenous copolyester based on greater than 50% of repeat units derived from caprolactone and having a melting temperature of at least about 40° C., a heat of fusion of at least about 15 J/g, and a number average molecular weight of at least about 30,000 Daltons. The present copolyester includes a central nitrogen atom derived from a nitrogenous initiator and repeat units derived from a comonomer mixture of from about 92 percent to about 98 percent by weight of caprolactone and from about 2 percent to about 8 percent by weight of glycolide. Preferably, the nitrogenous initiator is triethanolamine, although a variety of other nitrogen-containing initiators may be employed including N-methyl diethanolamine, hydroxyethyl pyridine, or hydroxyethyl piperidine.

In one preferred embodiment the present inventive copolyester may be employed as a coating composition for a metallic stent. Preferably, the coating composition also includes a bioactive compound, most preferably an antiproliferative agent.

In another preferred embodiment the present inventive copolyester may be formed into a monofilament suture.

In yet another preferred embodiment the present inventive copolyester may be formed into a microporous foam, which may be employed as a scaffold for tissue engineering.

Another aspect of the present invention is directed to providing a method for making essentially spherical, polymeric beads, which includes the steps of: providing a preliminary, cylindrical particle of a polymer having a glass transition temperature; suspending the cylindrical particle in a medium; heating the medium to a temperature above the glass transition temperature of the polymer, such that the particle assumes a shape having a minimum surface area; and cooling the particle, thereby stabilizing the shape. If the polymer also has a melting temperature, the present method requires that the medium is heated to a temperature above the glass transition temperature of the polymer and no greater than the melting temperature of the polymer. In one preferred embodiment the polymer is a polyester, preferably the present inventive copolyester. The present method may also include the step of agitating the heated medium, thereby enhancing heat transfer to the suspended particle. Although it may be a gas, preferably the medium is a liquid. One preferred medium is a concentrated, aqueous solution of inorganic salts. Also preferred as a medium for the present inventive method is glycerin. The present method is a preferred means for making an absorbable bead for plugging the end of a radiation therapy seed needle.

DETAILED DESCRIPTION OF THE PREFERRED EMBODIMENTS

This invention deals with crystalline, high molecular weight, nitrogenous copolyester compositions based on more than 50 percent of ε-caprolactone-derived repeat units. One aspect of this invention deals with a crystalline, nitrogenous copolyester composition with more than 50 percent of its mass derived from ε-caprolactone and exhibiting a $Tm \geq 40°$ C., heat of fusion ($\Delta H_f$), of $\geq 15$ J/g, and inherent viscosity (I.V.) in chloroform of $\geq 0.5$ dl/g. A more specific aspect of this invention deals with a crystalline nitrogenous copolyester composition made from a mixture of 95%±3% and 5%±3% caprolactone and glycolide, respectively, using triethanolamine as an initiator and stannous octoate as a catalyst to produce copolymers having the following properties: $Tm \geq 40°$ C., $\Delta H_f \geq 15$ J/g, I.V.$\geq 0.5$, molecular weight $\geq 30,000$ Da (as determined by GPC), and percent elongation, as a 0.1 mm compression-molded film, of $\geq 100\%$. Another aspect of this invention deals with a crystalline nitrogenous composition made by end-grafting caprolactone or a mixture of caprolactone, glycolide, and/or lactide onto a nitrogenous prepolymer made by reacting trimethylene carbonate with or without other comonomers, such as glycolide, lactide, p-dioxanone, ε-caprolactone, and 1,5-dioxapan-2-one, using a diamine or triethanolamine as the initiator and an organometallic catalyst. This is to produce a final copolymer containing more than 50 percent of its mass as ε-caprolactone derived sequences and having the following properties: $T_m \geq 40°$ C., $\Delta H_f \geq 15$ J/g, and I.V.$\geq 0.5$, molecular weight $\geq 30$ kDa (as determined by GPC), and percent elongation as a 0.1 mm, as a compression-molded film, of $\geq 100$ percent.

Another aspect of this invention deals with the use of one or more of the nitrogenous copolyester composition described in this invention as a coating for stents, including metallic endovascular ones, with or without one or more bioactive compound. Another specific aspect of this invention deals with the use of one or more of the compositions described in this invention as a coating of a metallic endovascular stent containing 0.1 percent to 70 percent of a bioactive compound that can display an antiproliferative activity towards smooth muscle cells. Another aspect of this invention deals with the use of one or more of the crystalline nitrogenous compositions subject of this invention to produce monofilament or multifilament yarns having a breaking strength of ≧30 kpsi or tenacity of ≧1.5 g/d, respectively, which can be used as highly compliant absorbable monofilament ligatures as in sutures, braided sutures, knitted fabric, woven fabric and/or other fibrous constructs for use as surgical and dental devices. Another aspect of this invention deals with the use of one or more of the crystalline nitrogenous compositions subject of this invention as continuous cell microporous foam in the form of sheets, microspheres, and thin-walled tubes. Another aspect of this invention deals with use of the copolymers subject of this invention as scaffolds for tissue engineering in the form of a fibrous construct or microporous foam. Another aspect of this invention deals with use of one or more of the crystalline nitrogenous compositions described in this invention for the production of microspheres, microbeads, or rods. These can be used as absorbable plugs to block the distal end of seed needles for use in conjunction with different protocols of radiation therapy.

Another aspect of this invention deals with the use of the nitrogenous compositions described herein in the production or assembling of (1) absorbable sealant coating for synthetic vascular grafts; (2) absorbable hemostatic device which may contain a potent hemostatic compound; (3) an absorbable or partially absorbable fibrous construct or foam for patching defective tissue or organs; and (4) a barrier device for sealing or plugging holes created in blood vessels and other biological conduits.

Another aspect of this invention deals with the process of converting rods or pellets made of one or more of the polymers, subject of this invention, into spherical, nearly spherical, or ellipsoidal articles for use as absorbable plugs to block the end of seed needles for use in conjunction with different protocols of radiation therapy, as in the case of prostate gland treatment. This process entails thermal transformation of cylinders to spheres and can be applied to particles of irregular morphology. The process of spheroidization or conversion of short cylinders into spheres, imperfect spheres, or ellipsoids entails suspending the cylindrical particles of the desired volume in a heated medium at a temperature approaching the polymer $T_m$, or slightly above it, to allow the particles to assume a volume with minimum surface area. This may be associated with partial melting of said particles or mass flow above the polymer $T_g$ for highly amorphous polymers. For practically amorphous rods, the medium is heated above the polymer $T_g$. To stabilize the new shapes, the medium can be cooled by quenching or by using a cold diluent. The types of heated medium and their temperatures are selected to prevent polymer dissolution or particle aggregation. The suspension medium may be subjected to ultrasonic or mechanical agitation to aid heat transfer and minimize the processing time. The heated medium may comprise a (1) non-reactive gas medium such as air, nitrogen, argon; (2) non-solvent (for polymer) type such as paraffin oil; (3) non-solvent (for polymer) of polyhalogenated liquids; (4) high concentration, aqueous solution of inorganic salts; (5) fluidized bed of solid microparticles made of an inorganic salt, silica, or fine sand; and (6) gel-like aqueous solution of non-reactive polymers such as polyvinyl pyrrolidone and polyvinyl alcohol.

Another aspect of this invention deals with the application of the spheroidization process subject of this invention to other amorphous and semicrystalline, absorbable polymers other than those which are described in this invention and more specifically, those comprising lactide-based sequences in their macromolecular chains.

Illustrative examples of the above noted embodiments are provided in the following examples:

EXAMPLE 1

Synthesis of High Molecular Weight 95/5 ε-Caprolactone/Glycolide Crystalline Nitrogenous Composition A mixture of ε-caprolactone (143 g, 1.254 mole) and glycolide (7.7 g, 0.066 mole) was charged into a predried reactor, equipped for mechanical stirring, under an anhydrous nitrogen atmosphere. To this was added triethanolamine (0.13 g, $8.71 \times 10^{-4}$ mole) as the initiator and a catalytic amount of stannous octoate (1.1 ml of a 0.2 M solution in toluene, $2.2 \times 10^{-4}$ mole). The system was heated at 40° C. under reduced pressure for at least 10 minutes and then purged with dry nitrogen. The charge was then heated to and kept at 160° C. while maintaining mechanical stirring until the resulting polymer was too viscous to stir. The polymerization was continued for 6 hours. At the conclusion of this period, the polymer was cooled, isolated, and ground. The ground polymer was dried at 40° C. under reduced pressure and characterized for identity by NMR and IR, thermal properties by DSC, and molecular weight using inherent viscosity and GPC. The GPC chromatograms indicated no significant level of residual monomer in the polymer. Analytical data of the polymer can be summarized as follows: $T_m$=50° C., $\Delta H_f$=67 J/g, I.V.=1.6, $M_n$(by GPC in THF)=121 kDa.

EXAMPLE 2

Purification of the 95/5 Copolymer of Example 1

To remove trace amounts of monomer and low molecular weight oligomers and to maximize polymer purity for use in stent coating, an acetone solution of the polymer was precipitated (under high shear) in an ice-water (using distilled water) bath. The precipitated polymer was dried to a constant weight in a laminar flow hood and then under reduced pressure at 40° C. The polymer purity was determined using NMR and GPC. The polymer molecular dimensions were recorded using GPC and I.V. and its $T_m$ was determined using DSC.

EXAMPLE 3

Preparation of a Film from the Polymer of Example 2

Using a laboratory Carver Press, the dried polymer was compression molded at 145° C. and a pressure of 3,000 lbs. to produce films having 0.1 mm thickness. The films were tested for percent elongation using a MiniBionix MTS Universal Tester at a strain rate of 0.5 mm/s. The molded film was shown to have a percent elongation prior to breaking of more than 200.

EXAMPLE 4

Preparation of a High Molecular Weight 93/7 ε-Caprolactone/Glycolide Crystalline Nitrogenous Copolymer The copolymer was prepared as described in Example 1 with the exception of using a 93/7 caprolactone/glycolide comonomer ratio. The analysis of the polymer was conducted as in Example 1 and the respective data can be summarized as follows: $T_m$=49° C., $\Delta H_f$=67 J/g, I.V.=1.6, $M_n$ (by GPC in THF)=109 kDa.

EXAMPLE 5

Preparation of Monofilament Yarn from 95/5 ε-Caprolactone/Glycolide Nitrogenous Copolymer A typical copolymer similar to that described in Example 1, having an I.V.=1.6 and $T_m$=50° C. was extruded at 185° C. into undrawn monofilaments using a ½" single-screw extruder. The monofilaments were drawn in two stages using a total draw ratio of 6×. The properties of the drawn monofilament are summarized below:

| | |
|---|---|
| Diameter = 0.22 mm | Linear tensile strength = 85 kpsi |
| Modulus = 350 kpsi | Knot strength = 60 kpsi |
| Elongation = 40% | |

EXAMPLE 6

Preparation of Absorbable Beads

A monofilament having a diameter of 1 mm was cut into 1 mm-long rods. The latter were suspended in about 50 percent aqueous solution of high molecular weight polyvinyl pyrrolidone (PVP). The gel-like medium containing the rods was heated with mild agitation at 90° C. until the rods acquired a spherical morphology. At this point the system was placed at 4° C. to stabilize the dimensions of the beads. These were isolated by diluting the PVP solution and filtration. The beads were rinsed with water and isopropyl alcohol and then dried under reduced pressure.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicants hereby disclose all sub-ranges of all ranges disclosed herein. These sub-ranges are also useful in carrying out the present invention.

What is claimed is:

1. A high molecular weight, crystalline nitrogenous suture including a co-polyester, the copolyester comprising:
   a central nitrogen atom derived from a nitrogenous, amine-bearing initiator;
   repeat units derived from a comonomer mixture comprising from about 92 percent to about 98 percent by weight of caprolactone and from about 2 percent to about 9 percent by weight of glycolide, the copolyester having a number average molecular weight of about 109 kDa; and
   wherein the polymerization of the copolyester is completed over a period of about 6 hours.

2. The suture set forth in claim 1 wherein the nitrogenous initiator comprises triethanolamine.

3. The suture set forth in claim 1 wherein the nitrogenous initiator comprises a member selected from the group consisting essentially of N-methyl diethanolamine, hydroxyethyl pyridine, and hydroxyethyl piperidine.

* * * * *